US011836831B2

(12) United States Patent
Berker et al.

(10) Patent No.: US 11,836,831 B2
(45) Date of Patent: Dec. 5, 2023

(54) METHOD FOR GENERATING AN IMAGE OF AN OBJECT FROM MEASUREMENT DATA (71) Applicant: Deutsches Krebsforschungszentrum, Heidelberg (DE)

(72) Inventors: Yannick Berker, Bensheim (DE); Marc Kachelrieß, Nuremberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 512 days.

(21) Appl. No.: 17/162,958

(22) Filed: Jan. 29, 2021

(65) Prior Publication Data
US 2021/0183117 A1    Jun. 17, 2021

Related U.S. Application Data (63) Continuation of application No. PCT/EP2019/070360, filed on Jul. 29, 2019.

(30) Foreign Application Priority Data
Jul. 30, 2018    (EP) .................................. 18186298

(51) Int. Cl.
*G06T 11/00*    (2006.01)
*A61B 6/03*    (2006.01)
*A61B 6/00*    (2006.01)

(52) U.S. Cl.
CPC ............ *G06T 11/005* (2013.01); *A61B 6/032* (2013.01); *A61B 6/037* (2013.01); *A61B 6/5205* (2013.01);
(Continued)

(58) Field of Classification Search
CPC ......... A61B 6/037; A61B 6/32; A61B 6/5205; A61B 6/5282; G06T 11/005; G06T 11/006; G06T 2211/408; G06T 2207/10081
See application file for complete search history.

(56) References Cited

U.S. PATENT DOCUMENTS

| 2003/0128801 A1* | 7/2003 | Eisenberg ............. A61B 6/466 378/19 |
| 2018/0078221 A1 | 3/2018 | Petersilka |
| 2018/0146935 A1 | 5/2018 | Song et al. |

OTHER PUBLICATIONS

Ogawa et al., Accurate Scatter Compensation using Neural Networks in Radionuclide Imaging, IEEE Transactions on Nuclear Science, vol. 40, No. 4, 1993, pp. 1020-1025.
(Continued)

*Primary Examiner* — Daniel G Mariam
(74) *Attorney, Agent, or Firm* — Bose McKinney & Evans LLP (57) ABSTRACT A method for training of a process for generating an image of an object from measurement data modified by scatter radiation. Individual sets of measured data are each made up of matrix elements. Each matrix element corresponds to an individual detector element that detects ionizing radiation. Signals measured by the individual detector elements in an energy bin are assigned as values for each matrix element. The individual sets of measured data and a template image are used as input for a procedure for determining a correction image for correcting a modification of the measured data by the scatter radiation. The preliminary image obtained using the individual sets of measured data is adjusted to the template. These steps are repeated until the deviation between the preliminary image and the template image is below a threshold. The procedure is used to generate the image of the object from the measurement data.

20 Claims, 4 Drawing Sheets (52) U.S. Cl.
CPC .......... *A61B 6/5282* (2013.01); *G06T 11/006* (2013.01); *G06T 2211/408* (2013.01)

(56) References Cited

OTHER PUBLICATIONS

Maksud et al., Artificial Neural Network as a Tool to Compensate for Scatter and Attenuation in Radionuclide Imaging, J Nucl Med, vol. 39, No. 4, 1998, pp. 735-745.

Xu et al., Deep residual learning in CT physics: scatter correction for spectral CT, 2017 Nuclear Science Symposium and Medical Imaging Conference, M-16-4, 14 pages, available under https://arxiv.org/abs/1708.04151.

Qian et al., Deep Learning Models for PET Scatter Estimations, NSS/MIC 2017, Atlanta, USA, 13 pages, available under https://www.eventclass.org/contxt_ieee2017/online-program/session?s=M-04#4237.

Maier et al., Deep Scatter Estimation (DSE): Accurate Real-Time Scatter Estimation for X-Ray CT Using a Deep Convolutional Neural Network, Journal of Nondestructive Evaluation (2018) 37:57, 9 pages, available under https://doi.org/10.1007/s10921-018-0507-z.

Ronneberger et al., U-Net: Convolutional Networks for Biomedical Image Segmentation, in: Navab N., Hornegger J., Wells W., Frangi A. (eds.), Medical Image Computing and Computer-Assisted Intervention—MICCAI 2015. MICCAI 2015. Lecture Notes in Computer Science, vol. 9351. Springer, pp. 234-241.

Fakhri et al., A New Scatter Compensation Method for Ga-67 Imaging Using Artificial Neural Networks, Nuclear Science Symposium Conference Record, 2000 IEEE Lyon, France Oct. 15-20, 2000, vol. 2, Jan. 1, 2000 (Jan. 1, 2000), pp. 13/48-13/52, XP055539196, US DOI: 10.1109/NSSMIC.2000.949989 ISBN: 978-0-7803-6503-2, pp. 799-801.

International Search Report and Written Opinion of the International Searching Authority, PCT/EP2019/070360, dated Oct. 21, 2019, 9 pages.

\* cited by examiner

Fig. 4

METHOD FOR GENERATING AN IMAGE OF AN OBJECT FROM MEASUREMENT DATA

RELATED APPLICATIONS

This application is a continuation of PCT/EP2019/070360, filed Jul. 29, 2019, which claims priority to EP 18 186 298.8, filed Jul. 30, 2018, the entire disclosures of both of which are hereby incorporated herein by reference.

BACKGROUND

This disclosure relates to a method for generating an image of an object from measurement data, a method for a training of a process for generating an image of an object from measurement data, and a computer program product comprising executable instructions for performing any one of these methods. As used herein, the methods according to this disclosure are computer-implemented methods. Herein, the measurement data were obtained by an imaging modality using ionizing radiation, wherein the measurement data were modified by scatter radiation. This disclosure may, particularly, be applied in the field of oncologic imaging; however, other applications are also possible.

Oncologic imaging, specifically for detecting suspicious changes in a body of a subject, specifically a patient, by using a non-invasive imaging modality is still a challenging task. Imaging modalities based on applying ionizing particles that are currently available for characterizing body parts include x-ray computed tomography (CT), single-photon emission computed tomography (SPECT), and positron emission tomography (PET).

In PET, a radioactive imaging agent, also denominated as "radiotracer" or simply "tracer," is routinely administered to the subject, specifically to the patient, wherein the radioactive imaging agent is designed for being distributed within the body of the subject and for leading to an emission of two photons of a well-defined energy of 511 keV per radioactive decay. A spatial distribution of the photons which have been emitted by the radioactive imaging agent within the body of the subject is recorded by a PET detector as PET data, wherein the recorded spatial distribution of the emitted photons is, subsequently, used for generating an image, wherein the image comprises a graphical representation of a particular property of the emitted photons in a relationship to a location of the assumed emission of the photons in the body of the subject or a part thereof. While the photons recorded in the PET detector are obtained from the decay of the positrons that are provided by the radiotracer, the photons which are detected in a CT or a SPECT detector are provided by x-rays in CT and by gamma rays in SPECT, respectively.

In order to be able to record the spatial distribution of the emitted photons, the PET detector comprises a plurality of detector elements which are, typically, arranged over a torus or a cylinder surrounding the object or at least a part thereof. Since the decay of the positrons results in a pair of emitted photons, the PET detector is, therefore, designed for detecting coincident pairs of the emitted photons, also denoted as "coincidences." This kind of information as detected by the PET detector is, subsequently, used as an input for image generation. Herein, the parameters which are, typically, measured for each photon comprise a spatial position of the detector element, a time of the recording of the photon, and a photon energy of the recorded photon.

The two photons which are, concurrently, emitted by the radioactive imaging agent travel in almost exactly opposite directions. Considering that each emitted photon travels along a straight line, a conclusion can be drawn that the two concurrently emitted photons have been emitted on a point in space along a line-of-response which connects the two detector elements of the PET detector which are involved in detecting the two concurrently emitted photons. However, due to an interaction between the emitted photons and matter, including but not limited to the body of the subject and the detector equipment, photon scattering may occur at one or more scattering objects, which results in a change of the direction of at least one of the travelling photons. As a result, the assumption of the line-of-response as indicated above does not hold for coincidences which include a scattered photon.

In addition, due to the interaction between the emitted photons and matter a partition of the energy of the involved photons is transferred to the scattering object. Consequently, the energy of a scattered photon is below 511 keV. As a result, the scattered photons and, thus, scattered coincidences which may be obtained from scattered photons can be separated in the PET detector by identifying the scattered coincidences due to their energy below 511 keV and removing the corresponding recordings, in particular by applying thresholding, specifically hardware or software thresholding, with respect to the photon energy as measured by the PET detector. However, in practice, measurement uncertainties which are related to energy measurements result in, still, accepting some scattered photons. Therefore, an additional approach is required, typically by using an adapted kind of computer algorithm, in order to be able to correct for the impact of those scattered coincidences which appear to be unscattered coincidences. The unscattered coincidences may also be denoted by the term "true coincidences."

Routinely, the additional approach for a correction of the spatial distribution of the photons as measured by the PET detector may apply estimating a number of the scattered coincidences and, subsequently, subtracting the estimated number of the scattered coincidences from the measured coincidences, whereby only the true coincidences are obtained. In an alternative approach, a scatter estimate can be added to a forward projection of an iterative quantitative image generation algorithm in order to obtain a more accurate representation of the physical imaging process, thus allowing for a more accurate graphical representation of a distribution of the radioactive imaging agent in the body of the subject. Thus, each additional approach requires a process of "scatter simulation" which comprises inputting a distribution of matter in the object, an assumed distribution of the radiotracer in image space, and a model of the imaging process, including but not limited to a geometry of the detector and scanning parameters of the detector, such as a duration of the acquisition, and, further outputting an estimated number of scattered coincidences in detector space.

A well-known approach to scatter estimation is single scatter simulation (SSS) which uses basic geometrical considerations as well as the Klein-Nishina equation in order to determine the spatial distribution of the scattered coincidences involving only one single scattered photon that has been scattered only once. However, since in practice, both photons of a coincidence may have been scattered and, moreover, may have been scattered multiple times, SSS cannot be accurate, such that a post-correction, for example a tail fitting, is required. Herein, the tail fitting relies on the assumptions that, firstly, without scatter correction, the generated image intensity outside of the patient is mostly based on the measured scatter which includes multiply-scattered photons and, secondly, that the spatial distributions of the single-scattered coincidences and the multiply-scattered coincidences are similar. Thus, a scale factor between the single-scattered coincidences and the multiply-scattered coincidences can be determined by matching the intensities of back-projected single-scattered coincidences with the intensities of back-projected measured coincidences, including multiply-scattered coincidences. However, it has been found out that this approach is prone to various errors and sensitivities, most of all towards an underlying patient outline and a count statistics of the PET data.

A further known approach to scatter estimation involves a Monte-Carlo simulation starting from the assumed distribution of the radiotracer, for example, from results obtained by using a previous distribution without scatter correction. By way of example, other methods, such as particle-tracking, have proved to be effective in generating accurate scatter distributions but have failed to be applicable in clinical practice due to a high computational demand.

In a further known approach the scatter estimation is performed by using a deep convolutional neural network (CNN), specifically, a particular convolutional neural network referred to as artificial neural network (ANN), wherein connectivity patterns between elements denoted by the term "neurons" have been inspired by an organization of an animal visual cortex. Again, the network can, preferably, be trained by using ground-truth data which have been generated by Monte-Carlo simulations, in a fashion that true coincidences, single-scattered coincidences and multiply-scattered coincidences can be simulated individually.

Ogawa, K., and Nishizaki N., *Accurate scatter compensation using neural networks in radionuclide imaging*, IEEE Transactions on Nuclear Science, vol. 40(4), 1993, pp. 1020-1025, describe for SPECT that a small, non-convolutional ANN can be used for determining scatter fractions for a single detector element (dexel), whereby any neighborhood of the dexel is not taken into account. Herein, photon measurements at multiple energies are used, however, only for a single dexel. It is emphasized here that although SPECT uses a measurement of individual photons, not of photon pairs, whereby collimation is provided mechanically rather than electronically, the problem of photon scattering remains the same.

Maksud, P., Fertil, B., Rica, C., El Fakhri, G., and Aurengo, A., *Artificial Neural Network as a Tool to Compensate for Scatter and Attenuation in Radionuclide Imaging*, J Nucl Med, vol. 39(4), 1998, pp. 735-745, also use a small, non-convolutional ANN for determining scatter fractions for a single detector element (dexel), wherein attenuation correction is included if data from opposing SPECT views are available. Herein, two multi-energy measurements from opposing dexels are input to the ANN in a similar fashion with photon pairs in PET. Differences include, firstly, that, due to mechanical collimation, the number of opposing dexels in SPECT is much smaller than the number of possible dexel pairs in PET and, secondly, that no dexel neighborhood is considered in the ANN since each dexel pair is treated individually.

S. Xu, P. Prinsen, J. Wiegert, and R. Manjeshwar, *Deep residual learning in CT physics: scatter correction for spectral CT*, 2017 Nuclear Science Symposium and Medical Imaging Conference, M-16-4, available under https://arxiv.org/abs/1708.04151, describes a development of a deep residual learning framework to address both issues of computation simplicity and object dependency. A deep convolution neural network is trained to determine the scatter distribution from the projection content in training data sets. In test cases of a digital anthropomorphic phantom and real water phantom, they demonstrated that, with much lower computing costs, the proposed network provides sufficiently accurate scatter estimation.

H. Qian, X. Rui, and B. De Man, *Deep Learning Models for PET Scatter Estimation*, NSS/MIC 2017, Atlanta, USA, available under https://www.eventclass.org/contxt_ieee2017/online-program/session?s=M-04#4237, describes a development of two convolutional neural networks (CNN) models for PET scatter estimation. A first model estimates the multiple scatter distribution from the single scatter distribution in an iterative estimation process. A second model directly predicts the scatter of an object from the emission and attenuation sinograms of the object. As a result, the neighborhood of a dexel is taken into account here.

A similar approach for CT is described by J. Maier, S. Sawall, M. Knaup, and M. Kachelrieß, *Deep Scatter Estimation (DSE): Accurate Real-Time Scatter Estimation for X-Ray CT Using a Deep Convolutional Neural Network*, Journal of Nondestructive Evaluation (2018) 37:57, available under https://doi.org/10.1007/s10921-018-0507-z. Deep scatter estimation (DSE) uses a deep convolutional neural network which is trained to reproduce the output of Monte Carlo simulations using only the acquired projection data as input. Once trained, DSE can be applied in real-time and yields highly accurate scatter estimates that differ by <3% from Monte Carlo scatter predictions. Further, DSE clearly outperforms kernel-based scatter estimation techniques and hybrid approaches as they are in use today.

SUMMARY

This disclosure teaches a method for generating an image of an object from measurement data, a method for a training of a process for generating an image of an object from measurement data, and a related computer program product comprising executable instructions, which provide an improvement with respect to known methods, specifically by at least partially avoiding their disadvantages. In particular, this disclosure teaches how to generate the image of the object from the measurement data in a more reliable manner.

As used in the present specification, the term "comprising" or grammatical variations thereof, are to be taken to specify the presence of stated features, integers, steps or components or groups thereof, but do not preclude the presence or addition of one or more other features, integers, steps, components or groups thereof. The same applies to the term "having" or grammatical variations thereof, which is used as a synonym for the term "comprising."

In general, this disclosure relates to a method for generating an image of an object from measurement data, wherein, prior to its performance, a method for a training of a process for generating the image of the object from the measurement data, is performed. As generally used, the terms "method," "process" or "procedure" refer to a sequence of individual steps that may be performed in any possible manner unless otherwise explicitly indicated. Herein, each "step" of the method refers to a particular set of instructions provided to be performed subsequently and or, if appropriate, concurrently.

The methods according to this disclosure are computer-implemented methods. As generally used, the term "computer-implemented method" refers to a method which involves a programmable apparatus, in particular, a computer, a computer network, or a readable medium carrying a program, whereby one or more of the features of this disclosure are performed by means of at least one program. Alternatively, the at least one program may be accessible by an apparatus being adapted to perform the respective method via a network, such as an in-house network or the internet. With particular regard to this disclosure, the present method can, thus, being performed on a programmable apparatus which is configured for this purpose, such as by providing a particular computer program. As a result, the present method may, as described below in more detail, particularly affect generating the an image of an object from measurement data, thereby providing highly reliable results by being able to remove modifications in the image caused by scatter radiation as far as possible.

In a first aspect of this disclosure, a computer-implemented method for a training of a process for generating an image of an object from measurement data is disclosed, wherein the measurement data were obtained by an imaging modality using ionizing radiation, wherein the measurement data were modified by scatter radiation. Herein, this method comprises at least the following steps a) to step c), wherein, however, additional steps may further be performed. Preferably, steps a) and b) may be performed in a sequential approach or a partially overlapping fashion, wherein, according to step c), steps a) and b) are repeated in this order until an indicated termination criterion is met. In particular, this method comprises the steps of:

a) providing at least two individual sets of measured data, wherein each of the sets of the measured data is provided as a matrix having a plurality of matrix elements, wherein each of the matrix elements corresponds to at least one individual detector element designated for detecting ionizing radiation, wherein a signal measured by the individual detector element in an energy bin is assigned as a value for each matrix element, wherein the individual sets of the measured data differ with respect to each other by their corresponding energy bin; and b) using the at least two individual sets of measured data and a template image as an input to a procedure for determining a correction image for a correction of a modification of the measured data by the scatter radiation, whereby the process is trained by adjusting a preliminary image obtained by using the at least two individual sets of measured data in the procedure to the template image, wherein the procedure comprises taking into account a neighborhood of each matrix element; and c) repeating steps a) and b) until a deviation between the preliminary image obtained by the process and the template image is below a threshold, whereby the procedure for determining the correction image for the correction of the modification of the measured data by the scatter radiation is obtained and applicable in the process for generating an image of an object from measurement data.

As generally used, the term "object" refers to any body having an extension in space that can be used as a sample for investigation purposes in at least one of an imaging modality as described below in more detail. In particular, the object may be a body of a subject, specifically the body of a patient, wherein the patient undergoes in a further step preceding step a) at least one selected imaging modality, especially, for diagnostic purposes. However, other kinds of objects, whether species in-vitro or in-vivo, organic or inorganic samples may also be used for the methods according to this disclosure.

As further generally used, the term "image of an object" refers to a representation, specifically a graphical representation, of at least a part of the object by a plurality of values, each of which represents a particular property of that part of the object, wherein each value links the particular property to an individual location within the corresponding part. In general, the image comprises a plurality of picture elements, usually, denoted by the term "pixel," wherein each of the pixels is corresponding to at least one of the individual detector elements. In general, the image may, preferably, be a two-dimensional representation of at least of the part of the object, wherein each of the values is, typically, placed in a two-dimensional matrix having columns and rows, thus, facilitating a visual perception of the image by a human. Alternatively, the image may be provided in form of a three-dimensional representation of at least part of the object, wherein each of the values may, typically, be placed in a three-dimensional matrix having planes, column and rows wherein a two-dimensional representation may be obtained by extracting an individual plane from the three-dimensional matrix. However, other kinds of images may also be feasible, such as images having a rotational, a polar, or a cylindrical symmetry. In particular, the images which are used for the methods herein comprise a graphical representation of a particular property of emitted photons in a relationship to a location of the assumed emission of the photons in the object, specifically, of a distribution of a radioactive imaging agent in the body of the subject. Herein, the particular property of emitted photons may be amplitude, intensity, or attenuation of the emitted photons as a signal being directly measured by a single detector element or as obtained from an evaluation of at least one signal obtained from a single detector element. However, further properties are feasible.

For this purpose, generating of an image may be preferred in which deviations of the graphical representation from the corresponding value at the respective location in the object may be small. By way of example, the deviations within the graphical representation may be below a threshold or a regression analysis, preferably a least square fitting algorithm, may be applied. However, other kinds of regression analysis may also be feasible. In particular, the image generation may be based on a scatter estimate which can be added to a forward projection of an iterative image generation algorithm in order to obtain a more accurate representation of the physical imaging process. As a result, an accurate graphical representation of a distribution of the radioactive imaging agent in the body of a subject may be acquired.

As indicated above, one of the methods according to this disclosure addresses training of a process for generating an image of an object from measurement data. As generally used, the term "training" indicates here that the desired process is determined during a training phase by providing a plurality of training data sets, wherein each training data set comprises a template image and at least two sets of measured data. Herein, each of the training data sets comprises data which were determined by using the imaging modality as described herein, wherein the template image is obtained as described below in more detail. For the purpose of training, the at least one training data set is iteratively applied during the training phase in order to improve the representation of the object.

Prior to step a), the measurement data are obtained by applying an imaging modality which uses ionizing radiation. As generally used, the term "imaging modality" refers to an investigation method, preferably a non-invasive investigation method, which is capable of providing an image of an object to be investigated as defined above. Herein, imaging modalities which are based on applying ionizing particles that are currently available for characterizing a body or a part thereof include x-ray computed tomography (CT), single-photon emission computed tomography (SPECT), and positron emission tomography (PET). Although the methods and devices are predominantly described herein by using the particular example of PET, they are mutatis mutandis applicable to other modalities which apply ionizing particles, such as CT or SPECT.

As already indicated above, in order to record an image that represents the spatial distribution of the emitted photons in PET, the detector comprises a plurality of detector elements which are, typically, arranged over a torus or a cylinder surrounding the object, such as the body of the subject, or at least a part thereof, whereas in SPECT and CT the plurality of the detector elements may be capable of rotating around the object. However, further arrangements of the plurality of the detector elements may be feasible. In general, the plurality of the detector elements is adapted to provide measurement data in form of individual sets of measured data, wherein each set of the measured data comprises a measurement value which was measured, preferably, for each of the detector elements. As a result, each value, which corresponds to the measurement value or is derived therefrom, links a particular property of the object to an individual location within the corresponding part of the object. However, due to an interaction between the emitted photons and scattering objects, specifically the investigated object and/or the detector equipment, photon scattering occurs, which results in a change of the direction of at least one of the travelling photons and, in addition, in a transfer of a partition of the energy of the involved photons to the scattering object. As a result, the image which is obtained in this fashion is, in general, modified by scatter radiation, wherein the term "scatter radiation" is related to various properties of scattering, including but not limited to an angle-dependent and/or energy-dependent intensity, which may be experienced by the radiation in a particular radiation device, such as a PET device. In addition, a modification of the image obtained in this fashion can, thus, comprise a reduction of a contrast and, further, a distortion of values assigned to pixel elements.

According to step a), at least two individual sets of measured data are provided which are used subsequently in step b) as described below in more detail as an input to a procedure for determining a correction image for a correction of a modification of the measured data by the scatter radiation. As used herein, the term "correction image" refers to a particular kind of image which is designated for the correction of the modification of the measured data by the scatter radiation. Herein, each individual set of the measured data comprises a plurality of values which may correspond to the signals that are obtained by the plurality of the detector elements, occasionally also denoted as "dexels," or at least a part thereof, being designated for detecting at least one property of the ionizing radiation provided by the emitted photons. For this purpose, each of the sets of the measured data is provided as a matrix as defined above, wherein the matrix has a plurality of matrix elements, wherein each of the plurality of the matrix elements corresponds to at least one, preferably exactly one, of the individual detector elements or dexels. Herein, the matrix may also include a list mode data format, in which detected photon pairs are stored together with additional related information, including but not limited to time, energy, or location (crystal index), as a one-dimensional matrix. However, further kinds of matrices may also be feasible.

In accordance with this disclosure, at least two, preferably 2 to 200 individual, more preferred 3 to 100, most preferred 4 to 20, individual sets of measured data are provided. Preferably, each of the at least two individual sets of the measured data differ with respect to each other by their corresponding energy bin, wherein two adjacent energy bins may, preferentially, not exhibit any overlap. However, as an alternative, as long as at least two of the individual sets of the measured data differ with respect to each other by their corresponding energy bin, other individual sets of the measured data may be provided for the same energy bin or for an overlapping energy bin. As generally used, the term "energy bin" or "energy window" refers to a section of an energy spectrum which is obtained for the measured radiation, wherein adjacent energy bins may, preferably, not exhibit any overlap. Due to the interaction between the emitted photons and matter, the energy of the involved photons may at least be partially transferred to the scattering object, whereas unscattered photons maintain their initial energy of emission. As a result, the energy spectrum, typically, shows a peak at the energy of the ionizing radiation and a generally reduced intensity towards lower energies. By way of example, due to the interaction between the emitted photons and matter in PET, the energy of the involved photons of 511 keV may at least partially be transferred to the scattering object, whereas unscattered photons maintain their initial energy of 511 keV. Further taking into account a width of the respective peaks, the energy spectrum of the scattered PET photons may, consequently, comprise a range of 0 keV to about 600 keV. Two or more, in particular 20 or more, or even 100 or more energy bins may be provided, thus, allowing a more specific training of the process for generating an image of the object from the measurement data.

The energy spectrum or a part thereof is, according to this disclosure, being divided into at least two individual ranges, whereby at least two bins are obtained, wherein the values that belong to a particular energy bin are considered as constituting the individual set of measured data for that particular energy bin. For this purpose, each of the detector elements may provide a signal which can be assigned to the respective energy bin, wherein a signal measured by the individual detector element within an energy bin is assigned as a value for each matrix element within the particular matrix being assigned to the respective energy bin. In general, the division of the energy spectrum can be performed in a manner that equally-spaced energy bins over at least a part of the energy spectrum or, as an a alternative, individually adapted energy bins may be provided. In a particularly preferred embodiment, the section of the energy spectrum as covered by each of the energy bins may extend below the peak of the ionizing radiation, which in the case of PET is 511 keV. By way of example, the energy spectrum of the scattered PET photons may, thus, be divided into the following three different bins extending from 460 keV to >340 keV, from 340 keV to >220 keV, and from 220 keV to 100 keV. Such a kind of division of the energy bins may be particularly advantageous since the energy bins covering at least a part of the energy spectrum below the peak of the ionizing radiation mainly comprises information about the scatter radiation. However, in an alternative embodiment, one of the sets of the measured data is obtained for an energy bin which may comprise the peak of the ionizing radiation and the at least one other set of measured data for at least one further energy bin whose energy range is below the peak of the ionizing radiation. By way of example, the energy spectrum of the scattered PET photons may, thus, be divided into the following four different bins extending from 550 keV to >450 keV, from 450 keV to >350 keV, from 350 keV to >250 keV, and from 250 keV to 150 keV. This alternative embodiment may, advantageously, allow providing a relationship of scatter radiation with respect to unscattered radiation. However, other kinds dividing the energy spectrum into two or more energy bins may be applicable.

According to step b), the at least two individual sets of the measured data, each of which comprises a matrix of matrix elements, and a template image are used as an input to scatter correction, i.e., a procedure for determining the correction image for the correction of the modification of the measured data by the scatter radiation, which may, preferably, comprise a process for determining the estimation of the scatter radiation. By way of example, the at least two individual sets of the measured data may be obtained by PET as the imaging modality, wherein another imaging modality, such as SPECT or CT may also be feasible. As used herein, the "template image" refers to a graphical representation of the image for correction of the modification of the measured data by scatter radiation. Herein, the template image may be generated by using a method for determining an estimation of scatter radiation, wherein a use of a Monte Carlo photon transport code is particularly preferred. This code simulates photon histories and can, thereby, simulate all relevant physical effects. Due to scattering nature, however, such calculations are rather small. Alternatives, which are computationally less demanding but also less accurate, include, in increasing degree of approximation, a use of a Boltzmann transport equation, a consideration of only first-order scatter, a use of pre-trained scatter kernels that propagate through a CT volume, a use of pre-trained scatter kernels that operate on an x-ray image and a use of simple empirical methods, such as a subtraction of a constant value from the measured intensities. Instead of estimating scatter by simulations, measurements for estimating scatter can also be performed, including a use of additional detector rows that do not record primary radiation and, thus, provide a scatter estimate at a periphery of an imaging field, a use of moving or stationary beam blockers which locally block small regions from recording primary radiation, and a use of primary modulators imposing a high frequency pattern on the primary radiation not being recorded on the scattered radiation. The correction image for correction of the modification of the measured data by scatter radiation can also be an image representing the scatter-corrected measurement data after subtraction of a scatter estimation determined by one of the methods mentioned before.

In a preferred embodiment, a so-called "deep scatter estimation" may be used for the process for determining the estimation of the scatter radiation may use. As used herein, the term "deep scatter estimation" comprises an architecture which is a slight modification of a U-net being developed by Ronneberger O., Fischer P., Brox T. (2015), *U-Net: Convolutional Networks for Biomedical Image Segmentation*, in: Navab N., Hornegger J., Wells W., Frangi A. (eds.), *Medical Image Computing and Computer-Assisted Intervention—MICCAI 2015*. MICCAI 2015. Lecture Notes in Computer Science, Vol. 9351. Springer. As described in J. Maier, cited above, additional average pooling layers are added to the U-net of Ronneberger et al., thus, leading to an increased performance of validation data.

A further approach for scatter correction, i.e., the correction of the modification of the measured data by the scatter radiation, could combine the process of scatter estimation with the process of subtracting the results of the scatter estimation by directly estimating the scatter-corrected coincidences.

In a further preferred embodiment of this disclosure, at least one additional image can be used as an additional input for the procedure for determining the correction image for the correction of the modification of the measured data by the scatter radiation, wherein the additional image comprises additional pixels, wherein each of the additional pixels corresponds to a value related to an attenuation of the radiation by the object. For this purpose, the attenuation can, in particular, be selected from the group consisting of an attenuation correction factor, an inverse of the attenuation correction factor, and a logarithm of the attenuation correction factor. By way of example, data acquired from a second modality, such as attenuation sinograms of the object, can be used for the attenuation correction. However, further kinds of attenuation data may also be feasible, such as transmission measurements with radio nuclides, magnetic resonance tomography (MRT), or using a method such as joint reconstruction of attenuation and activity in PET or SPECT measurements. In a preferred embodiment, attenuation maps can be generated, from which images in measurement space may, subsequently, be obtained. In addition, it appears to be feasible to provide a combination of measurement data with attenuation data, such as a multiplication thereof.

As already indicated above, the process for generating the image of the object from the measurement data is trained during step b). For this purpose, a preliminary image as generated by using the at least two individual sets of measured data in the procedure for determining the correction image for the correction of the modification of the measured data by the scatter radiation, in particular in the process for determining the estimation of the scatter radiation, is adjusted to the template image. Herein, at least one parameter may be used which may be designated for determining any difference between the generated preliminary image and the template image.

In a particularly preferred embodiment of this disclosure, the correction image for the correction of the modification of the measured data may be generated by using a machine learning technique. As generally used, the term "machine learning technique" refers to a computer-implemented process, by which an apparatus is designed during a "training phase" to determine from at least one set of input data a set of parameters which allows generating at least one set of output data which is capable of approximating at least one template set of output data, wherein the determining is achieved in an iterative process designated to consecutively improve the approximating of the at least one template set of output data. After the training phase, the set of parameters is used for generating at least one further set of output data by using at least one further set of input data, whereby the obtained output data is reasonably expected to approximate 'true' output data in the same manner as achieved during the training phase. In this fashion, a more accurate representation of the physical imaging process can be obtained during the training phase. Thus, after the training phase, the desired accurate graphical representation of the distribution of the radioactive imaging agent in the body of the subject may be acquired.

In a preferred embodiment, the scatter estimation may, thus, be performed by using a deep convolutional neural network (CNN), specifically, a particular convolutional neural network referred to as artificial neural network (ANN), wherein connectivity patterns between elements denoted by the term "neurons" have been inspired by an organization of an animal visual cortex. Herein, the network can, preferably, be trained by using ground-truth data which have been generated by simulations, such as Monte-Carlo simulations, in a fashion that true coincidences, single-scattered coincidences and multiply-scattered coincidences can be treated individually. However, other kinds of processes for determining the estimation of the scatter radiation, such as a non-convolutional ANN, may also be applicable.

For the purpose of training, the at least one training data set is during the training phase iteratively applied according to step c) by repeating steps a) and b), preferably in this order, until a deviation between the preliminary image of the object as generated by the process and the template image is below a threshold. Thus, steps a) and b) may be repeated for at least one training data set, preferably for a large number of training data sets, wherein each of the training data sets comprises at least two individual sets of measured data and a template image. Preferably, 1,000 to 1,000,000,000 training data sets, more preferred 10,000 to 100,000,000 training data sets, in particular 30,000 to 1,000,000 training data sets, such as 100,000 training data sets, may be used for this purpose. In this manner, the desired process for generating the image of the object is obtained, which is, as described below in more detail, subsequently, applicable for being used for generating an unknown image of an object.

In accordance with this disclosure, the procedure for determining the correction image for the correction of the modification of the measured data by the scatter radiation comprises taking into account a neighborhood of each of the matrix elements as comprised by the matrices generated by the individual sets of measured data. As generally used, the term "neighborhood" refers to a further matrix element within the same matrix which has a relationship to a particular matrix element with regard to a distance between the detector elements corresponding to the matrix elements. Herein, a particular matrix element and a further matrix element have a direct neighborhood in an event in which no additional detector element is located between the two adjacent detector elements corresponding to the matrix elements. However, the neighborhood can also include further matrix elements the corresponding detector elements of which may be separated from the detector element corresponding to the particular matrix element by only one additional detector element. In addition, the "neighborhood" may be even more generalized by taking in to account further matrix elements the corresponding detector elements of which may be separated from the detector element corresponding to the particular matrix element by more than one additional detector element. By way of example, in a two-dimensional matrix as described above the neighborhood of the particular matrix element may comprise those matrix elements whose coordinates differ by ±1 with respect to one or both axes. By way of example, the neighborhood can, thus, comprise the nine matrix elements which surround the particular matrix element in the two-dimensional matrix. However, further kinds of neighborhoods may also be feasible.

In addition, since at least two individual sets of measured data are provided as at least two individual matrices, each matrix having a plurality of matrix elements, the at least two individual matrices may be provided in form of subsequent layers in which the matrix elements of adjacent layers may also be considered as being in the neighborhood. By way of example, a particular matrix element in a particular matrix generated from a particular individual set of measured data may not only have matrix elements in the neighborhood within the same particular matrix as described above but also within at least two adjacent matrices similarly generated from a other individual sets of measured data. Again, the "neighborhood" may even be more generalized by taking in to account further matrix elements which may be separated from the particular matrix elements by one or by more than one additional layer of further matrix elements. In an alternative view, the subsequent layers may be considered as forming a three-dimensional matrix, in which the neighborhood of the particular matrix elements may comprise those matrix elements whose coordinates differ by ±1 with respect to one, two or three of the three axes.

Further, at least one additional set of additional measured data can, additionally, be used in a similar manner, wherein the additional measured data were obtained by the imaging modality using ionizing radiation under a different angle with respect to the at least two individual sets of measured data. As generally used, the angle refers to an orientation of a two-dimensional representation of the measured data with respect to a reference angle, such as provided by an axis of symmetry of the detector elements. However, further kinds of reference angles may also be feasible.

As used herein, the term "taking into account a neighborhood of a matrix element" refers to involving a value of at least one adjacent matrix element to the value of each of the matrix elements when the training of the process for generating the image of the object from measurement data and, subsequently, the method for generating the image of the object from measurement data is performed. Hereby, the involving a value of at least one adjacent matrix element to the value of each of the matrix elements may be performed by assigning shared weight to groups of adjacent matrix elements, such as described below exemplary in more detail. By way of example, the same shared weight may be assigned to matrix elements having an identical grade of neighborhood, such as having the same number of differing coordinates. However, other kinds of assignments of the shared weights to the matrix elements may also be feasible.

In a further aspect of this disclosure, a computer-implemented method for generating an image of an object from measurement data is disclosed, wherein the measurement data were obtained by an imaging modality using ionizing radiation, wherein the measurement data were modified by scatter radiation. Herein, this method comprises at least the following steps a), d) and e), wherein, however, additional steps may further be performed. Preferably, steps a) and d) may be performed in a sequential approach or a partially overlapping fashion, wherein, according to step e), the generated image of the object is, subsequently, output. In particular, this method comprises the steps of:

a) providing at least two individual sets of measured data, wherein each of the sets of the measured data is provided as a matrix having a plurality of matrix elements, wherein each of the matrix elements corresponds to at least one individual detector element designated for detecting ionizing radiation, wherein a signal measured by the individual detector element in an energy bin is assigned as a value for each matrix element, wherein the individual sets of the measured data differ with respect to each other by their corresponding energy bin;

d) using the at least two individual sets of measured data as an input to a procedure for determining a correction image for the correction of the modification of the measured data by the scatter radiation as obtained during a training phase, whereby the image of the object is generated by using the at least two individual sets of measured data in the procedure, wherein the procedure comprises taking into account a neighborhood of each matrix element; and e) outputting the image of the object generated from the measurement data.

It is emphasized here that step a) of the present method is identical to step a) as provided elsewhere herein with respect to the method for a training of a process for generating an image of an object from measurement data. Consequently, the description with regard to step a) is equally applicable here.

According to step d), only the at least two individual sets of measured data are used here as an input to a process for generating an image of an object from measurement data as obtained during the training phase. As a result, the image of an object is generated by using the at least two individual sets of measured data in the procedure for determining the correction image for the correction of the modification of the measured data by the scatter radiation as described elsewhere in more detail, wherein, again, the procedure for determining the correction image for the correction of the modification of the measured data by the scatter radiation comprises taking into account a neighborhood of each matrix element as described elsewhere herein in more detail.

According to step e), the generated image of the object is output, preferably to a display device, such as a monitor or a display comprised by a different apparatus. However, a purely electronic transmission of the generated image of the object to a further unit may also be feasible. As generally used, the terms "output" and "outputting" refer to providing an item as desired by the corresponding process or step, here the generation of the image of the object by the respective method step, as a result, in particular for a subsequent use. In addition, the output may include a graphical representation of the correction image for correction of the modification of the measured data by scatter radiation which can be used in step e) for generating the image of the object, in which the scatter radiation has been more accurately considered.

For further details concerning the method for generating an image of an object from measurement data, reference may be made to the description of the method for a training of a process for generating an image of an object form measurement data.

In a further aspect, this disclosure refers to a computer program product which comprises executable instructions for performing at least one of the methods, preferably both methods, according to this disclosure. For this purpose, a computer program may comprise instructions provided by means of a computer program code which are capable of performing any or all of the steps of the methods according to this disclosure and, thus, to establish a generation of an image of an object when implemented on a computer or a data processing device. The computer program code may be provided on a data storage medium or a separate device such as an optical storage medium, e.g., on a compact disc, directly on a computer or data processing device, or via a network, such as an in-house network or the internet. For further details concerning the computer program product, reference may be made to the methods according to this disclosure as disclosed elsewhere herein.

The methods and the computer program product according to this disclosure provide considerable advantages over known methods and devices. In particular, the methods according to this disclosure are, in contrast to S. Xu and H. Qian as cited above, capable of using energy information from different energy windows as input in order to obtain an output of an image for correction of the modification of the measured data by scatter radiation in each of at least one energy windows. As a result, the generation of the image of the object from measurement data obtained by an imaging modality using ionizing radiation, wherein the measurement data were modified by scatter radiation, is more accurate.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
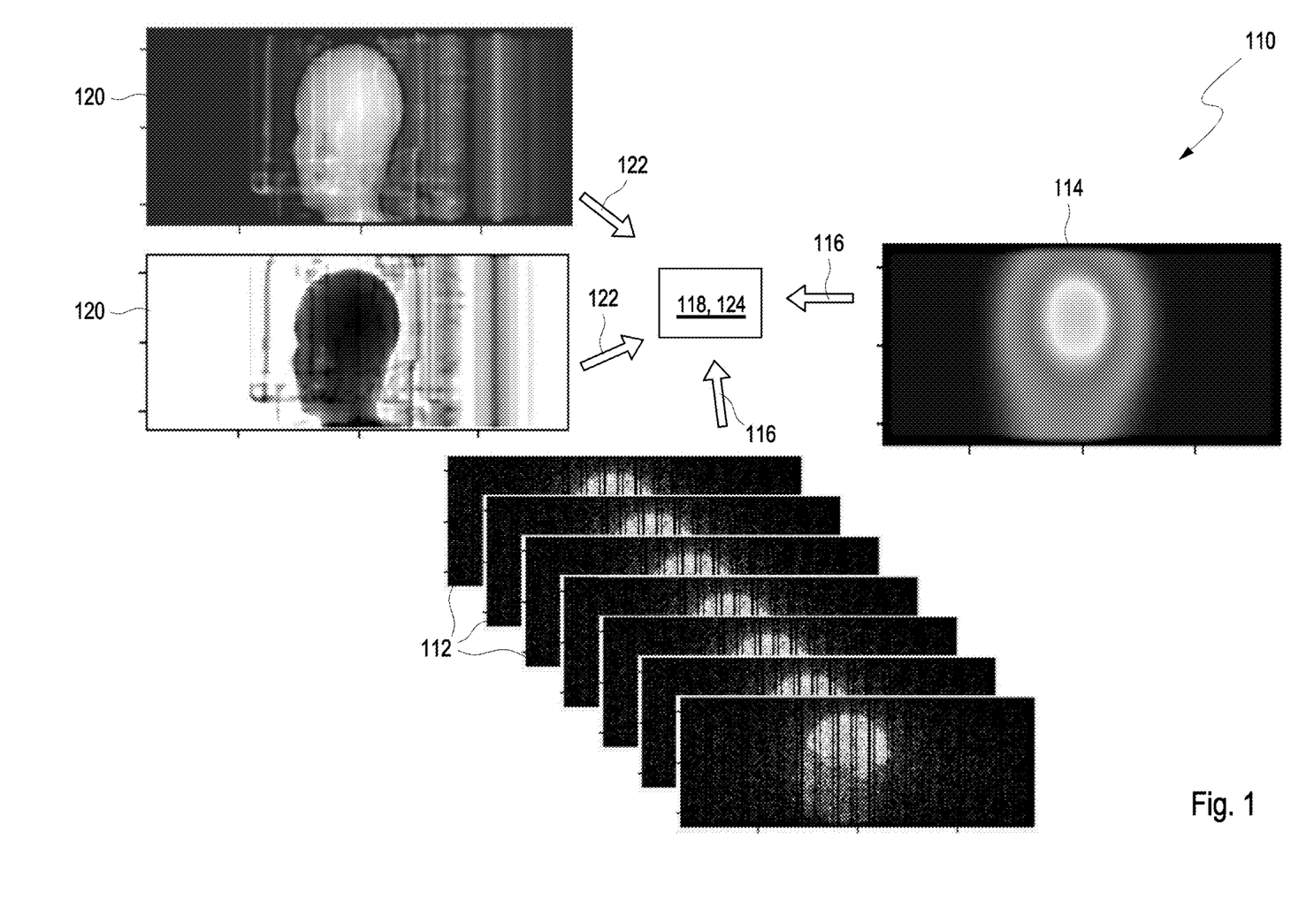
FIG. 1 schematically illustrates a preferred example of a method for a training of a process for generating an image of an object from measurement data according to this disclosure.

FIG. 1 schematically illustrates a preferred example of a computer-implemented method 110 for a training of a process for generating an image of an object from measurement data according to this disclosure. In this exemplarily embodiment, six individual sets of measured data are provided, according to step a), in form of two-dimensional matrices 112. However, other kinds of matrices may also be feasible. Herein, each of the matrices 112 has a plurality of matrix elements being arranged in a two-dimensional matrix having columns and rows, thus, facilitating a visual perception of the matrix 112 by a human. A value, such as a numerical value, is assigned to each of the matrix elements, which may graphically be presented, for example, by using a grey scale or a color scale. Each of the values corresponds to a value of a signal, which may be selected from an amplitude, an intensity, or an attenuation, being provided by an individual detector element which is designated for detecting ionizing radiation impinging the object.

In the particular example of FIG. 1, the matrices 112 were obtained by applying positron emission tomography (PET) as an imaging modality which uses ionizing radiation. In the examples as presented herein the methods and devices are described by using the particular example of PET; still they are mutatis mutandis applicable to other modalities which apply ionizing particles, including but not limited to single-photon emission computed tomography (SPECT) and x-ray computed tomography (CT). Thus, in the present example of FIG. 1, each of the matrices 112 represent a spatial distribution of emitted photons which are detected by using a plurality of individual detector elements, typically, arranged over a torus or a cylinder surrounding the object, such as the body of the subject, or at least a part thereof.

However, due to an interaction between the emitted photons and scattering objects, specifically the investigated object and/or detector equipment, photon scattering occurs, which results in a change of a direction of at least one of the travelling photons and, in addition, in a transfer of a partition of the energy of the involved photons to the scattering object. As a result, each of the matrices 112 obtained in this fashion is, thus, generally modified by scatter radiation, resulting in a possible change of the value assigned to the matrix elements of the matrices 112.

In the exemplary embodiment of FIG. 1 six individual sets of measured data are provided in the form of the matrices 112 in accordance with this disclosure. However, a different number of matrices as indicated above may also be feasible. As explained below with respect to FIG. 3 in more detail, each of the six individual sets of the measured data differs with respect to each other by their corresponding energy bin, wherein of the each energy bins, also denoted as "energy window," refers to a section of an energy spectrum being obtained for the measured radiation.

As further illustrated in FIG. 1, the six matrices 112 as the individual sets of the measured data and a template image 114, which has been obtained in this particular example by using a Monte Carlo photon transport code, are used, according to step b), as an input 116 to a procedure 118 for determining a correction image 128 for a correction of a modification of the measured data by scatter radiation. In addition, two additional images 120 are provided in this exemplary embodiment as an additional input 122 for the procedure 118 for determining the correction image 128 for the correction of the modification of the measured data by the scatter radiation. As further depicted in FIG. 1, the two additional images 120 comprise additional pixels, wherein each of the additional pixels corresponds to a value related to an attenuation of the radiation by the object. For this purpose, the attenuation can, in particular, be selected from the group consisting of an attenuation correction factor, an inverse of the attenuation correction factor, and a logarithm of the attenuation correction factor.

Upon receiving of the six matrices 112 and the two additional images 120, the process for generating an image of an object from measurement data is, further according to step b), trained in a training phase 124 by adjusting a preliminary image as generated by using the input data comprising the six matrices 112 and the two additional images 120 in the procedure 118 for determining the correction image 128 for the correction of the modification of the measured data by the scatter radiation to the template image 114. As explained below with respect to FIG. 4 in more detail, the procedure 118 for determining the correction image 128 for the correction of the modification of the measured data by the scatter radiation comprises taking into account a neighborhood of each of the additional pixels.

Figure 2:
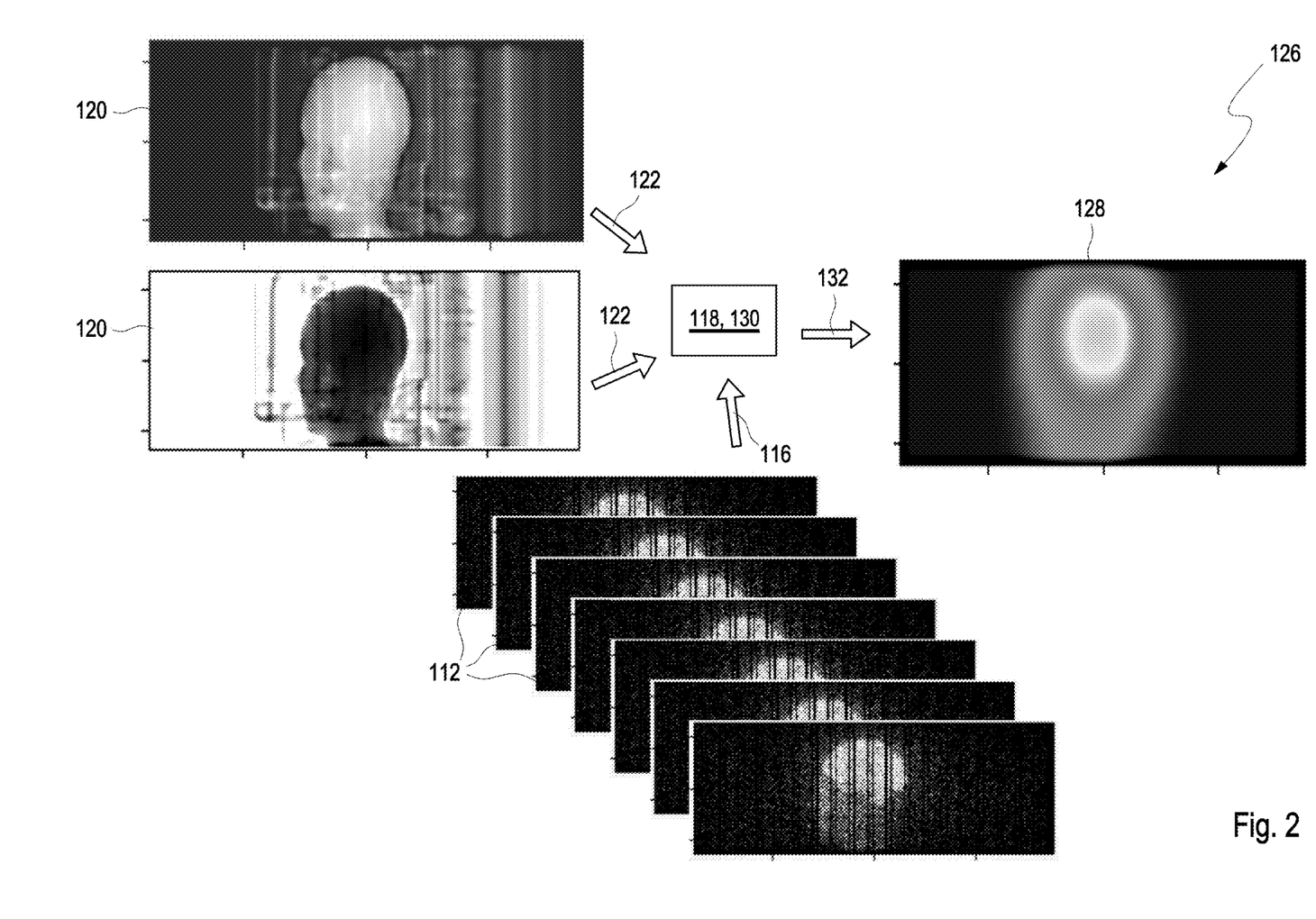
FIG. 2 schematically illustrates a preferred example of a method for generating an image of an object from measurement data according to this disclosure.

Herein, steps a) and b) are, in accordance with step c), repeated until a deviation between the preliminary image as generated from the six individual sets of the measured data and the template image 114 is below a threshold. For this purpose, a set of parameters is determined during a training phase 124 from the input data comprising the six matrices 112 and the two additional images 120, thus, generating output data which are compared to the template image 114 until a predetermined grade of approximation may be achieved. Herein, for determining the set of the parameters an iterative process is used which designed for consecutively improving the grade of approximation of the output data to the template image 114. The set of parameters obtained in this fashion is after the training phase 124, as illustrated in FIG. 2, used for generating the desired accurate image of a distribution of the radioactive imaging agent in the object. As explained below with respect to FIG. 5 in more detail, the scatter estimation may, thus, be performed by using a deep convolutional neural network (CNN) in this particular embodiment.

As a result of applying the method 110 for the training of the process for generating an image of an object from measurement data as schematically illustrated in FIG. 1, the process for generating an image of an object from measurement data is obtained. According to this disclosure, this process for generating an image of an object from measurement data is now available and can, subsequently, be used in a method 126 for a generating an image of an object from measurement data as explained below with respect to FIG. 2 in more detail.

FIG. 2 schematically illustrates a preferred example of the computer-implemented method 126 for generating an image of an object from measurement data according to this disclosure. Herein, the image was obtained by applying positron emission tomography (PET) as the imaging modality which is using ionizing radiation, wherein the image was modified by scatter radiation as described above in more detail.

In the exemplary embodiment of FIG. 2, six individual sets of measured data are provided, according to step a), in the form of the matrices 112, wherein, however, a different number of matrices 112 as indicated above may also be feasible. As shown below in FIG. 3 in more detail, each of the individual sets of the measured data differs with respect to each other by their corresponding energy bin, each of the energy bins or energy windows referring to a section of an energy spectrum within which the radiation was measured by the individual detector elements designated for detecting ionizing radiation.

As further illustrated in FIG. 2, the six matrices 112 as the individual sets of the measured data of the object are used, according to step d), as the input 116 to the process for generating an image of an object from measurement data as obtained in the method 110 for the training of the generating an image of an object from measurement data as further described above with respect to FIG. 1, wherein the same procedure 118 for determining the correction image 128 for the correction of the modification of the measured data by the scatter radiation as developed during the training phase 124 is used in a performance phase 130 here.

As additionally depicted in FIG. 2, the two additional images 120 are, again, provided in this exemplary embodiment as the additional input 122 for the procedure 118 for determining the correction image 128 for the correction of the modification of the measured data by the scatter radiation. Herein, the two additional images 120 comprise additional pixels, wherein each of the additional pixels corresponds to a value related to an attenuation of the radiation by the object. As explained below with respect to FIG. 4 in more detail, the procedure 118 for determining the correction image 128 for the correction of the modification of the measured data by the scatter radiation, which is also employed here, comprises taking into account the neighborhood of each of the additional pixels.

As further shown in FIG. 2, the procedure 118 for determining the correction image 128 for the correction of the modification of the measured data by the scatter radiation as developed in the training phase 124 provides in the performance phase 130 a graphical representation 128 of the scatter radiation as output 132 which can be used, according to step e), for generating the image of the object in which the scatter radiation has been more accurately considered. In this fashion, the desired accurate distribution of the radioactive imaging agent within the object, such as within the body of the subject, may, thus, be acquired.

Figure 3:
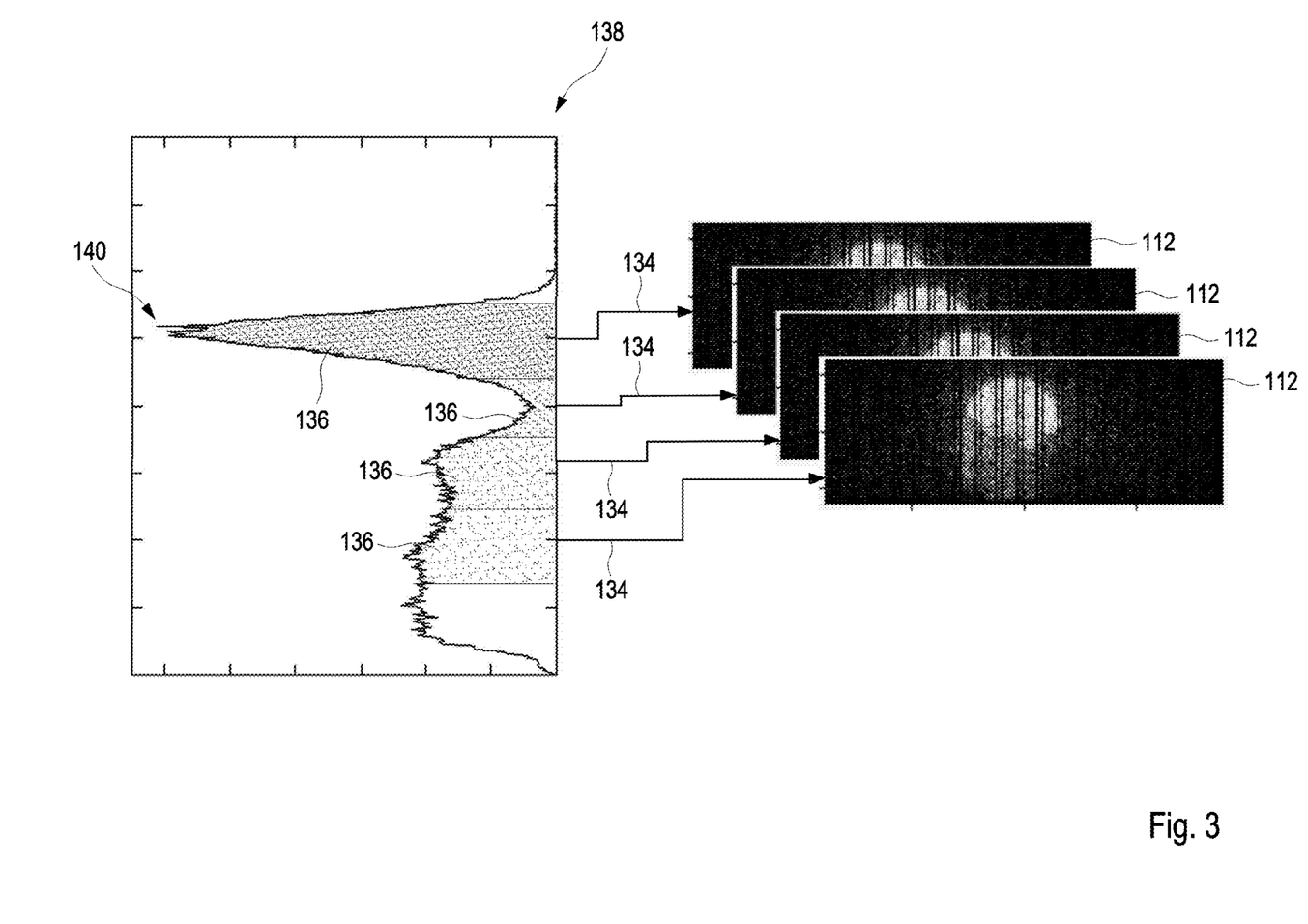
FIG. 3 schematically illustrates four individual sets of measured data, each of the sets being a matrix having a plurality of matrix elements, wherein the four individual sets differ by their corresponding energy bin.

FIG. 3 schematically illustrates an exemplary embodiment for providing four matrices 112 for the four individual sets of measured data as the input 116 to the process for generating an image of an object from measurement data as described above with respect to FIGS. 1 and 2 in more detail. Herein, each of the four matrices 112 has, again, a plurality of matrix elements. As indicated by the arrows 134, each of the four matrices 112 comprises data which are acquired for a corresponding energy bin 136, which refers to a section of an energy spectrum 138 that is obtained for the measured radiation.

Due to the interaction between the emitted photons and matter in PET, the energy of the involved photons of 511 keV may at least be partially transferred to the scattering object, whereas unscattered photons maintain their initial energy of 511 keV. As a result, the energy spectrum 138, typically, shows an energy peak 140 at the 511 keV which corresponds to the energy of the ionizing radiation in PET and a generally reduced intensity towards lower energies. Further taking into account a width of the respective peak 140, the energy spectrum of the scattered PET photons may, consequently, comprise a range of 0 keV to about 600 keV.

In the exemplary embodiment as depicted in FIG. 3, the energy spectrum 138 of the scattered PET photons is, thus, divided into the four different bins 136, wherein adjacent energy bins 136 do, in this particular example, not exhibit any overlap. Herein, the respective bins extend from 550 keV to >450 keV, from 450 keV to >350 keV, from 350 keV to >250 keV, and from 250 keV to 150 keV. However, other kinds dividing the energy spectrum 138 into 2 to 200, more preferred 3 to 100, most preferred 4 to 20, energy bins 136 may be applicable.

It is emphasized that, in the exemplary embodiment of FIG. 3, one of the matrices 112 is obtained for the energy bin 136 which comprises the energy peak 140 of the ionizing radiation at 511 keV for PET, whereas the three other matrices 112 correspond to further energy bins 136 whose energy range is below the energy peak 140 of the ionizing radiation. This embodiment may be chosen for be able to provide a relationship of the scatter radiation with respect to the unscattered radiation.

However, in an alternative embodiment (not depicted here), the section of the energy spectrum 138 which is covered by the energy bins 136 only extend below the energy peak 140 of the ionizing radiation, which in the case of PET is 511 keV. By way of example, the energy spectrum 138 of the scattered PET photons may, thus, be divided into the following three different bins 138 that extend from 460 keV to >340 keV, from 340 keV to >220 keV, and from 220 keV to 100 keV. This kind of division of the energy bins 136 may be particularly advantageous since the energy bins 138 covering the energy spectrum 138 below the energy peak 140 of the ionizing radiation mainly comprises information about the scatter radiation.

Figure 4:
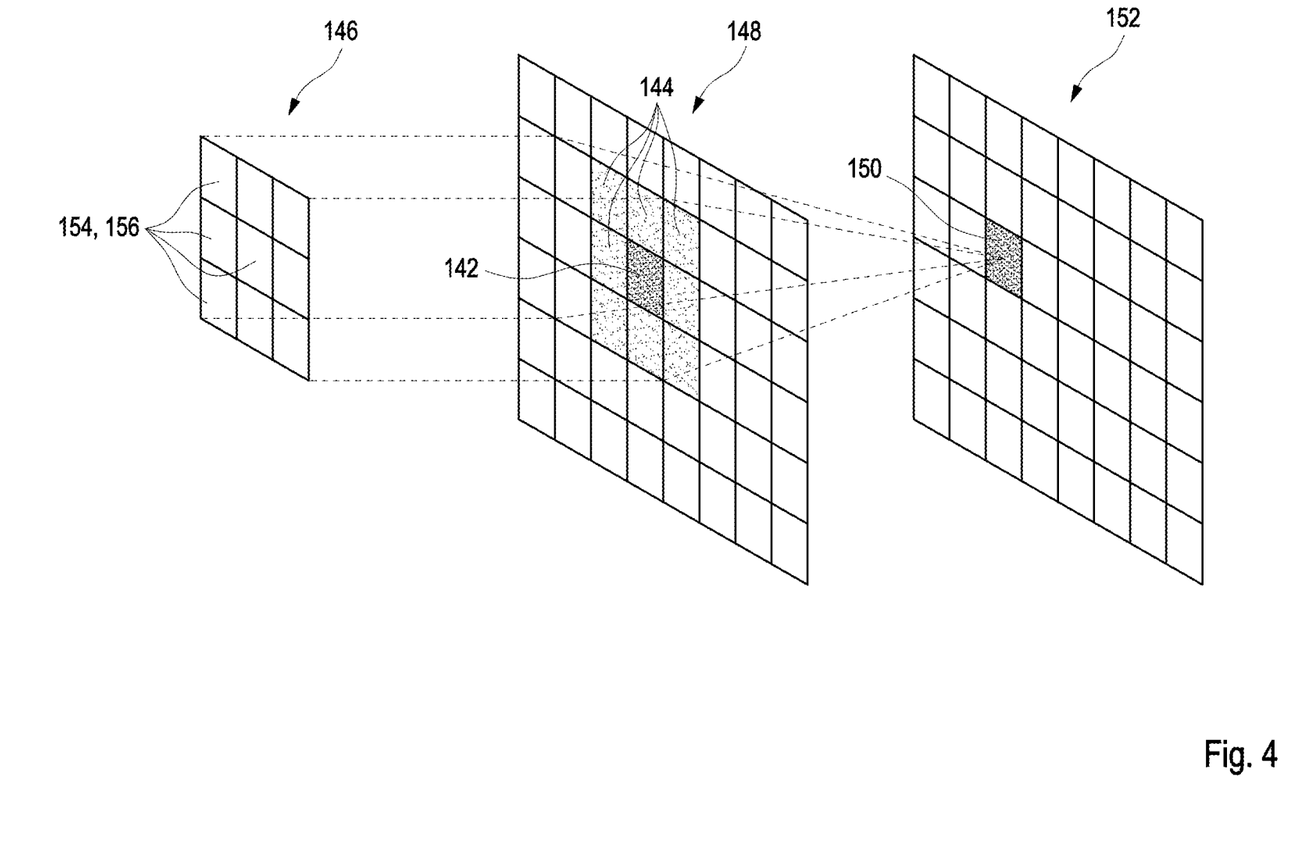
FIG. 4 schematically illustrates a preferred embodiment of a procedure for determining a correction image for a correction of a modification of the measured data by scatter radiation taking into account a neighborhood of each matrix element.

FIG. 4 schematically illustrates a preferred embodiment of the procedure 118 for determining the correction image 128 for the correction of the modification of the measured data by the scatter radiation taking into account a neighborhood of each matrix element 142. For this purpose, not only a value of each of the matrix elements 142 may be involved but, preferably, also values of one or more adjacent matrix elements 144 when the training of the process for generating an image of an object from measurement data and, subsequently, the method 126 for generating an image of an object from measurement data is performed. In the exemplary embodiment of FIG. 3, a kernel 146 having a 3×3 number of matrix elements is applied to an input matrix 148 in order to generate each weighted matrix element 150 as comprised by an output matrix 152. Hereby, each of a weighing matrix element 154 of the kernel 146 may carry a shared weight 156 which can be applied to the each of the matrix elements 142 including the one or more adjacent matrix elements 144. However, further kinds of kernels 146 may also be feasible.

In addition to the illustration of FIG. 3, in which the matrix element 142 and the adjacent matrix elements 144 are located in a direct neighborhood, the neighborhood that may be taken into account according to this disclosure can also include further matrix elements which can be separated from the matrix element 142 by one or more additional pixels (not depicted here). Further, since at least two individual matrices 112 differing by their energy bin 136 are provided during step a), wherein each of the individual matrices 112 has a plurality of matrix elements 142, the at least two individual matrices 112 can be considered as subsequent layers in which the matrix elements of adjacent layers can also assume neighborhood. Thus, the neighborhood can be more generalized (not depicted here) by taking into account further matrix elements that may be located in an adjacent layer with respect to the matrix element 142, or further separated from the matrix element 142 by one or by more additional layers of further matrix elements. As a result, the shared weight 156 which can be applied to the each of the matrix elements 142 can include at least one of the adjacent matrix elements 144 from the same layer within then same energy bin 136, from an adjacent layer having an adjacent energy bin 136 or even from a further layer having a further energy bin 136. Consequently, the procedure 118 for determining the correction image 128 for the correction of the modification of the measured data by the scatter radiation which is designated for taking into account the neighborhood of each matrix element 142 can provide a more accurate estimation of the scatter radiation, thus, resulting in a more accurately generation of the image of the object.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 method for a training of a process for generating an image of an object from measurement data
112 Matrix
114 template image
116 Input
118 procedure for determining a correction image for a correction of a modification of the measured data by scatter radiation
120 additional image
122 additional input
124 training phase 126 method for generating an image of an object from measurement data
128 correction image for a correction of a modification of measured data by scatter radiation
130 performance phase
132 Output
134 Arrow
136 energy bin
138 energy spectrum
140 energy peak
142 matrix element
144 adjacent matrix element
146 kernel
148 input matrix
150 weighed matrix element
152 output matrix
154 weighing matrix element
156 shared weight

What is claimed is:

1. A method for training of a process for generating an image of an object from measurement data that is obtained with an imaging modality using ionizing radiation, and the measurement data is modified by scatter radiation, the method comprising:
   a) providing at least two individual sets of measured data, each set comprising a matrix having matrix elements, each matrix element corresponding to at least one individual detector element configured for detecting ionizing radiation, wherein a signal measured by the individual detector element in an energy bin is assigned as a value for each matrix element, wherein the individual sets of the measured data differ with respect to each other by their corresponding energy bin;
   b) using the at least two individual sets of measured data and a template image as an input to a procedure for determining a correction image for correcting a modification of the measured data by the scatter radiation, whereby the process is trained by adjusting a preliminary image obtained by using the at least two individual sets of measured data to the template image, wherein the procedure comprises taking into account a neighborhood of each matrix element; and
   c) repeating steps a) and b) until a deviation between the preliminary image obtained by the process and the template image is below a threshold, whereby the procedure for determining the correction image can be implemented in generating the image of the object from the measurement data.

2. The method of claim 1, wherein the procedure for determining the correction image for the correction of the modification of the measured data by the scatter radiation comprises a process for determining an estimation of the scatter radiation.

3. The method of claim 1, wherein steps a) and b) are repeated for 1,000 to 1,000,000,000 training data sets, each training data set comprising at least two individual sets of measured data and a template image.

4. The method of claim 1, wherein each of the sets of measured data is measured in an energy bin, wherein the energy in the energy bin is below an energy peak of the ionizing radiation.

5. The method of claim 1, wherein one of the sets of the measured data is measured in an energy bin which comprises the energy peak of the ionizing radiation and the at least one other set of measured data is measured in a further energy bin below the energy peak of the ionizing radiation.

6. The method of claim 1, wherein 2 to 200 individual sets of measured data differing with respect to their energy bin are provided.

7. The method of claim 1, wherein the neighborhood of each matrix element within each of the matrices related to the individual sets of measured data is taken into account.

8. The method of claim 1, wherein the neighborhood of each matrix element between at least two of the matrices related to the individual sets of measured data is taken into account.

9. The method of claim 1, wherein the neighborhood of each matrix element is taken into account by involving a value of at least one adjacent matrix element to the value of each of the matrix elements.

10. The method of claim 1, wherein at least one additional set of additional measured data is used as an additional input for the process, wherein the additional measured data were obtained by the imaging modality using ionizing radiation under a different angle with respect to the at least two individual sets of measured data.

11. The method of claim 1, wherein at least one additional image obtained by a second imaging modality is used as an additional input, wherein the additional image comprises additional matrix elements, each additional matrix element corresponding to a value related to attenuation of the radiation by the object, wherein the additional image is used independently or in a combination with at least one of the sets of the measurement data.

12. The method of claim 1, wherein the procedure for determining the correction image for a correction of a modification of the measured data by the scatter radiation comprises using a convolutional neural network (CNN).

13. The method of claim 1, wherein the imaging modality is selected from positron emission tomography (PET), single-photon emission computed tomography (SPECT), and x-ray computed tomography (CT).

14. A non-transitory computer readable medium having stored thereon computer-executable instructions for performing the method of claim 1.

15. A method for generating an image of an object from measurement data that is obtained with an imaging modality using ionizing radiation and wherein the measurement data is modified by scatter radiation, the method comprising:
   providing at least two individual sets of measured data, wherein each set comprising a matrix having matrix elements, each matrix element corresponding to at least one individual detector element configured for detecting ionizing radiation, wherein a signal measured by the individual detector element in an energy bin is assigned as a value for each matrix element, wherein the individual sets of the measured data differ with respect to each other by their corresponding energy bin;
   using the at least two individual sets of measured data as an input to a procedure for determining a correction image for the correction of the modification of the measured data by the scatter radiation as obtained by the method of claim 1, whereby the image of the object is generated by using the at least two individual sets of measured data in the procedure, wherein the procedure comprises taking into account a neighborhood of each matrix element; and
   outputting the image of the object generated from the measurement data.

16. The method of claim 15, wherein each of the sets of measured data is measured in an energy bin, wherein the energy in the energy bin is below an energy peak of the ionizing radiation.

17. The method of claim 15, wherein one of the sets of the measured data is measured in an energy bin which comprises the energy peak of the ionizing radiation and the at least one other set of measured data is measured in a further energy bin below the energy peak of the ionizing radiation.

18. The method of claim 15, wherein 2 to 200 individual sets of measured data differing with respect to each other by their energy bin are provided.

19. The method of claim 15, wherein the imaging modality is selected from positron emission tomography (PET), single-photon emission computed tomography (SPECT), and x-ray computed tomography (CT).

20. A non-transitory computer readable medium having stored thereon computer-executable instructions for performing the method of claim 15.

* * * * *